(12) United States Patent
Yoshida et al.

(10) Patent No.: US 7,122,697 B2
(45) Date of Patent: Oct. 17, 2006

(54) METHOD FOR PRODUCING CARBAMATES AND METHOD FOR PRODUCING ISOCYANATES

(75) Inventors: Tsutomu Yoshida, Ibaraki (JP); Masaaki Sasaki, Ibaraki (JP); Satoshi Kuroiwa, Fukuoka (JP); Fumiaki Hirata, Ibaraki (JP)

(73) Assignee: Mitsui Takeda Chemicals, Inc., Tokyo (JP)

( * ) Notice: Subject to any disclaimer, the term of this patent is extended or adjusted under 35 U.S.C. 154(b) by 754 days.

(21) Appl. No.: 10/327,180

(22) Filed: Dec. 24, 2002

(65) Prior Publication Data

US 2003/0125579 A1 Jul. 3, 2003

(30) Foreign Application Priority Data

Dec. 28, 2001 (JP) ...................... 2001-398911

(51) Int. Cl.
*C07C 261/00* (2006.01)

(52) U.S. Cl. ...................... 560/157; 560/338

(58) Field of Classification Search .............. 560/24, 560/31, 36, 345
See application file for complete search history.

(56) References Cited

U.S. PATENT DOCUMENTS

| | | | | |
|---|---|---|---|---|
| 3,763,217 | A | * 10/1973 | Brill | .................... 560/24 |
| 3,919,279 | A | 11/1975 | Rosenthal et al. | |
| 4,003,938 | A | 1/1977 | Koenig et al. | |
| 4,290,970 | A | 9/1981 | Merger et al. | |
| 4,330,479 | A | 5/1982 | Merger et al. | |
| 4,395,565 | A | 7/1983 | Romano et al. | |
| 5,731,458 | A | 3/1998 | Dahmer et al. | ........... 560/345 |
| 5,773,643 | A | 6/1998 | Yagii et al. | ........... 560/345 |
| 5,789,614 | A | 8/1998 | Yagii et al. | |
| 5,914,428 | A | 6/1999 | Yagii et al. | |

FOREIGN PATENT DOCUMENTS

| | | |
|---|---|---|
| CA | 1 166 649 | 5/1984 |
| EP | 0 391 473 | 10/1990 |
| EP | 0 902 014 | 3/1999 |
| JP | 47-11562 | 6/1972 |
| JP | 57-82361 | 5/1982 |
| JP | 6-128215 | 5/1994 |
| JP | 6-172292 | 6/1994 |
| JP | 7-165696 | 6/1995 |
| WO | 87/05600 | 9/1987 |

OTHER PUBLICATIONS

Database Crossfire Beilstein Online! Beilstein Institut zur Förderung der Chemischen Wissenschaften, Frankfurt am Main, DE; retrieved from Beilstein *Database accession No. rid 199668 XP 002236978 \*abstract\**.

Database Crossfire Beilstein Online! Beilstein Institut zur Förderung der Chemischen Wissenschaften, Frankfurt am Main, DE; retrieved from Beilstein *Database accession No. rid 318418 XP 002236979 \*abstract\**.

Database Crossfire Beilstein Online! Beilstein Institut zur Förderung der Chemischen Wissenschaften, Frankfurt am Main, DE; retrieved from Beilstein *Database accession No. rid 996900 XP 002236980 \*abstract\**.

Database Crossfire Beilstein Online! Beilstein Institut zur Förderung der Chemischen Wissenschaften, Frankfurt am Main, DE; retrieved from Beilstein *Database accession No. rid 906312 XP 002236981 \*abstract\**.

Database Crossfire Beilstein Online! Beilstein Institut zur Förderung der Chemischen Wissenschaften, Frankfurt am Main, DE; retrieved from Beilstein *Database accession No. rid 2076662 XP 002236982 \*abstract\**.

Database Crossfire Beilstein Online! Beilstein Institut zur Förderung der Chemischen Wissenschaften, Frankfurt am Main, DE; retrieved from Beilstein *Database accession No. rid 997581 XP 002236983 \*abstract\**.

Database Crossfire Beilstein Online! Beilstein Institut zur Förderung der Chemischen Wissenschaften, Frankfurt am Main, DE; retrieved from Beilstein *Database accession No. rid 996905 XP 002236984 \*abstract\**.

Database Crossfire Beilstein Online! Beilstein Institut zur Förderung der Chemischen Wissenschaften, Frankfurt am Main, DE; retrieved from Beilstein *Database accession No. rid 3306051 XP 002237043 \*abstract\**.

Database Crossfire Beilstein Online! Beilstein Institut zur Förderung der Chemischen Wissenschaften, Frankfurt am Main, DE; retrieved from Beilstein *Database accession No. rid 2675661 XP 002237044 \*abstract\**.

Database Crossfire Beilstein Online! Beilstein Institut zur Förderung der Chemischen Wissenschaften, Frankfurt am Main, DE; retrieved from Beilstein *Database accession No. rid 1831701 XP 002237045 \*abstract\**.

(Continued)

*Primary Examiner*—Johann R. Richter
*Assistant Examiner*—Karl Puttlitz
(74) *Attorney, Agent, or Firm*—Wenderoth, Lind & Ponack, L.L.P.

(57) ABSTRACT

A method for producing carbamates that enables carbamates to be produced at low costs, with high selectivity and high yield, and in a simple manner, and a method for producing isocyanates that enables isocyanates industrially used to be produced by using the carbamates obtained by the carbamates producing method. Nonaromatic amine selected from the group consisting of aliphatic amine, alicyclic amine, and aralkyl amine is allowed to react with alkylaryl carbonate to thereby produce carbamates. Also, the carbamates thus obtained are thermally decomposed to thereby produce isocyanates. When carbamates are produced in this method, alkyl carbamates can be obtained with high selectivity and at high yield by using simple equipment. Also, when isocyanates are produced in this method, polyisocyanates used industrially as the raw material of polyurethane can be produced in a simple manner and with efficiency.

5 Claims, No Drawings

OTHER PUBLICATIONS

Database Crossfire Beilstein Online! Beilstein Institut zur Förderung der Chemischen Wissenschaften, Frankfurt am Main, DE; retrieved from Beilstein *Database accession No. rid 998442 XP 002237046* *abstract*.

Database Crossfire Beilstein Online! Beilstein Institut zur Förderung der Chemischen Wissenschaften, Frankfurt am Main, DE; retrieved from Beilstein *Database accession No. rid 9121229 XP 002237047* *abstract*.

U. Heubaum et al., "Optically Active Diazo Compounds, Diazocamphane", J. Amer. Chem. Soc. vol. 52, pp. 5070–5078, (Dec. 1930).

P.A. Berlin et al., "Molecular Organization of Reactants in Solution and Kinetic Relationships in Aminolysis of Carbon–Containing Compounds", J. Gen. Chem. USSR (English transl.), vol. 60–92, pp. 1909–1915, (1990).

\* cited by examiner

METHOD FOR PRODUCING CARBAMATES AND METHOD FOR PRODUCING ISOCYANATES

BACKGROUND OF THE INVENTION

1. Field of the Invention

The present invention relates to a method for producing carbamates and a method for producing isocyanates by using the carbamates produced by the method for producing carbamates.

2. Description of the Prior Art

Alkyl carbamates are organic compounds useful as raw materials of medicines, agricultural chemicals and the like; raw materials of a variety of fine chemicals; reagents for analysis of alcohols; and industrial raw materials used for various purposes.

A variety of methods for producing alkyl carbamates are known, including (1) a method of reacting isocyanate with alcohol, (2) a method of reacting chloroformate ester with amine in the presence of base, (3) a method of reacting phosgene with alcohol and amine, (4) a method of reacting urea with alcohol, (5) a method of reacting dimethyl carbonate with formamide, and (6) a method of reacting dialkyl carbonate with amine.

In recent years, many studies have been made for the uses of the alkyl carbamates as raw materials for producing isocyanates without using any phosgene.

Isocyanates is an organic compound containing an isocyanate group and is in wide use as raw materials of polyurethanes. Isocyanates is produced industrially by reacting amine with phosgene (Phosgenation). However, phosgene is highly toxic, corrosive and inconvenient in handling. In recent years, as an alternative to the phosgenation, a variety of methods for producing isocyanates economically have been proposed, according to which after carbamates are prepared from amine by using dialkyl carbonate, the carbamates obtained are thermally decomposed to thereby produce isocyanates (e.g. Japanese Laid-open (Unexamined) Patent Publications No. 7(1995)-165696, No. 6(1994)-172292, and No. 9(1997)-249633).

The methods for producing the alkyl carbamates cited above have the following disadvantages, however. The method (1) has the disadvantage that an irritating isocyanate must be handled as raw material and accordingly careful handling is required. The method (2) has the disadvantage that a base of a number of moles equal to or more than equimolar must be used. The method (3) has the disadvantages that phosgene is highly toxic and corrosive and that a base must be used in the reaction. The methods (4) and (5) have the disadvantage that the reaction must be done at high temperature or high pressure.

In the method (6), dimethyl carbonate is used as dialkyl carbonates (which is well known from Japanese Patent Publication No. Sho 51 (1976)-33095, Japanese Laid-open (Unexamined) Patent Publication No. 57(1982)-82361, and U.S. Pat. No. 4,395,565, for example). In this method, dimethyl carbonate is allowed to react with amine in the presence of a Lewis-acid, a lead, titanium or zirconium catalyst, or an alcoholate of alkali metal or alkali earth metal. The examples of this method show, however, that the rate of reaction is generally slow and also a N-methyl compound as a by-product is easily produced by the reaction. Due to this, the method (6) has the disadvantage that it is hard to provide improvement in space time yield (STY) of carbamates.

On the other hand, for example, Japanese Laid-open (Unexamined) Patent Publication No. Sho 64(1989)-85956 describes, as a method which suppresses the N-methylation reaction, the method by adding amine and alcoholate catalyst of alkali metal or alkali earth metal continuously or intermittently.

However, since this method requires a large amount of alcoholate catalyst for producing carbamates at high yields, production costs increase unavoidably. In addition, since the catalyst is neutralized, a large amount of salt is produced and resultantly a considerable burden is put on the recovery and purification of carbamates.

Further, an alternative method using carbonates has been proposed, for example, by Japanese Laid-open (Unexamined) Patent Publication No. Hei 6(1994)-128215 which teaches the method of producing an alkyl carbamate from alkyl aryl carbonate and aromatic amine. In this method, a nitrogen-containing heterocyclic compound is used as the catalyst. However, this method has the disadvantage that a large amount of the catalyst is required and improvement in yield cannot be attained.

In the methods for producing isocyanates previously mentioned, after carbamates are prepared from amine by using dialkyl carbonate, the carbamates obtained are thermally decomposed. However, as described, for example, in the examples of Japanese Laid-open (Unexamined) Patent Publication No. Sho 64(1989)-85956, when a base catalyst is heated together with carbamates, carbamates are changed further and are changed into an unintended high boiling material. Due to this, the neutralization process is unavoidable. As a matter of fact, prior to the thermal decomposition process of carbamates, it is necessary that the residual base catalyst in carbamates is neutralized by adding a phosphoric acid and the phosphoric acid excessively added is eliminated by washing.

SUMMARY OF THE INVENTION

It is an object of the present invention to provide a method for producing carbamates that enables carbamates to be produced in a simple manner at low costs with high selectivity and high yield, and to provide a method for producing isocyanates that enables isocyanates using industrially to be produced by using the carbamates obtained by the carbamates producing method.

The present invention provides a method for producing carbamates, wherein nonaromatic amine selected from the group consisting of aliphatic amine, alicyclic amine, and aralkyl amine is allowed to react with alkyl aryl carbonate as is expressed by the following general formula (1):

$$R^1OCOOR^2 \qquad (1)$$

(where $R^1$ represents an alkyl group and $R^2$ represents an aryl group that may have a substituent group).

In the method for producing carbamates of the present invention, it is preferable that the alkyl aryl carbonate is methylphenyl carbonate. Also, it is preferable that crude material containing at least 1 weight % of alkyl aryl carbonate obtained by an ester exchange reaction of dialkyl carbonate with phenol or derivative thereof is used as the alkyl aryl carbonate.

It is preferable that the nonaromatic amine is at least one compound selected from the group consisting of 1,6-hexamethylenediamine, isophorone diamine, 1,3-bis(aminomethyl)cyclohexane, 1,4-bis(aminomethyl)cyclohexane, 4,4'-methylenebis(cyclohexaneamine), 2,5-bis(aminomethyl)bicyclo[2,2,1]heptane, 2,6-bis(aminomethyl)

bicyclo[2,2,1]heptane, 1,3-bis(aminomethyl)benzene and 1,4-bis(aminomethyl)benzene. The nonaromatic amine may be amino acid and derivative thereof.

Further, the present invention provides a method for producing isocyanates which comprises the step of producing carbamates by reacting nonaromatic amine selected from the group consisting of aliphatic amine, alicyclic amine, and aralkyl amine with alkyl aryl carbonate expressed by the following general formula (1), and the step of producing isocyanates by thermally decomposing the carbamates obtained:

$$R^1OCOOR^2 \quad (1)$$

(where $R^1$ represents an alkyl group and $R^2$ represents an aryl group that may have a substituent group).

The method for producing carbamates of the present invention enables alkyl carbamates to be produced with high selectivity and at high yield simply by substantially blending nonaromatic amine and alkylaryl carbonate. Besides, since the producing method of the present invention requires no complicated after-treatment process, the carbamates can be produced at low costs and with efficiency. In addition, this producing method enables crude material containing alkylaryl carbonate to be used as alkylaryl carbonate.

Also, the method for producing isocyanates of the present invention enables polyisocyanates industrially used as raw material of polyurethane to be produced in a simple manner and with efficiency.

DETAILED DESCRIPTION OF THE PREFERRED EMBODIMENTS

In the following, a method for producing carbamates ('carbamate' is also referred as 'carbamic acid ester') of the present invention will be detailed. According to a method for producing carbamates of the present invention, nonaromatic amine selected from the group consisting of aliphatic amine, alicyclic amine, and aralkyl amine is allowed to react with alkyl aryl carbonate as is expressed by the following general formula (1):

$$R^1OCOOR^2 \quad (1)$$

(where $R^1$ represents an alkyl group and $R^2$ represents an aryl group that may have a substituent group).

The nonaromatic amine used in the present invention is an amino-group-containing organic compound having at least one primary or secondary amino group and having no amino group directly bonded to an aromatic ring and selected from the group of aliphatic amine, alicyclic amine, and aralkyl amine. The amino-group-containing organic compound may contain in the molecular structure -a stable bond or functional group, such as an ether, a thioether, an ester, a sulfonic and a carbonyl group, and a halogen atom.

Aliphatic amines that may be used include, for example, aliphatic primary normal or branched monoamines, such as methylamine, ethylamine, n-propylamine, iso-propylamine, butylamine, pentylamine, hexylamine, n-octylamine, 2-ethylhexylamine, decylamine, dodecylamine, and octadecylamine, aliphatic secondary monoamines of carbon number in the range of 2–20, such as dimethylamine, diethylamine, N-methylethylamine, di-n-octylamine, and N-methylcyclopentylamine, aliphatic diamines, such as 1,2-diaminoethane, 1,3-diaminopropane, 1,4-diaminobutane, 1,5-diaminopentane, 1,6-hexamethylenediamine, 1,7-diaminoheptane, 1,8-diaminooctane, 1,9-diaminononane, 1,10-diaminodecane, 1,12-diaminododecane, 2,2,4-trimethylhexamethylene diamine, 2,4,4-trimethylhexamethylene diamine, tetramethylene diamine, 1,12-diaminododecane, and 1,2-bis(aminoethylthio)ethane, aliphatic triamines, such as 1,2,3-triaminopropane, triaminohexane, triaminononane, triaminododecane, 1,8-diamino-4-aminomethyloctane, 2,6-diaminocaproic acid 2-aminoethylester, 1,3,6-triaminohexane, 1,6,11-triaminoundecane, triaminocyclohexane, and 3-aminomethyl-1,6-aminohexane, and amino acids, such as arginine, β-alanine, alanine, sarcosine, ornithine, γ-aminobutyric acid, α-aminoisobutyric acid, glycine, valine, norvaline, leucine, isoleucine, threonine, serine, methionine, aspartic acid, glutamic acid, glutamine, ricin, hydroxyricin, histidine, cysteine, and aspartic acid. These amino acids may be amino acids whose side-chain functional group is protected or may be racemic mixture containing optical isomer, or derivatives thereof, such as ester or salt thereof.

The aliphatic amines include, for example, amino-group-containing polyoxyalkylene compounds, such as polyoxypropylene diamine, and amino-group-containing polysiloxane compounds.

Alicyclic amines that may be used include, for example, alicyclic primary monoamines, such as cyclopropylamine, cyclobutylamine, cyclopentylamine, cyclohexylamine, and hydrogenated toluidine, alicyclic secondary monoamines, such as N-methylcyclopentylamine, alicyclic diamines, such as diaminocyclobutane, isophorone diamine (3-aminomethyl-3,5,5-trimethylcyclohexylamine), 1,2-diaminocyclohexane, 1,3-diaminocyclohexane, 1,4-diaminocyclohexane, 1,3-bis(aminomethyl)cyclohexane, 1,4-bis(aminomethyl)cyclohexane, 4,4'-methylenebis (cyclohexaneamine), 2,5-bis(aminomethyl)bicyclo[2,2,1] heptane, 2,6-bis(aminomethyl)bicyclo[2,2,1]heptane, hydrogenated 2,4-toluene diamine, and hydrogenated 2,6-toluene diamine, and amino acids, such as proline and hydroxylproline. These amino acids may be amino acids whose side-chain functional group is protected or may be racemic mixture containing optical isomer, or derivatives thereof, such as ester or salt thereof.

Aralkyl amine that may be used include, for example, aralkyl primary monoamines, such as benzylamine, aralkyl secondary monoamines, such as N-mehylbenzylamine, aralkyl diamines, such as 1,3-bis(aminomethyl)benzene and 1,4-bis(aminomethyl)benzene, and amino acids, such as phenylalanine, tyrosine, tryptophan, and phenylglycine. These amino acids may be amino acids whose side-chain functional group is protected or may be racemic mixture containing optical isomer, or derivatives thereof, such as ester or salt thereof.

Among these nonaromatic amines, diamines supplying as precursors of poly(di)isocyanates that are used industrially, such as 1,6-hexamethylene diamine, isophorone diamine, 1,3-bis(aminomethyl)cyclohexane, 1,4-bis(aminomethyl) cyclohexane, 4,4'-methylenebis(cyclohexaneamine), 2,5-bis (aminomethyl)bicyclo[2,2,1]heptane, 2,6-bis(aminomethyl) bicyclo[2,2,1]heptane, 1,3-bis(aminomethyl)benzene and 1,4-bis(aminomethyl)benzene, are preferably used.

These nonaromatic amines may be used singly or in combination of two or more.

The alkylaryl carbonate used in the present invention is expressed by the following general formula (1):

$$R^1OCOOR^2 \quad (1)$$

(where $R^1$ represents an alkyl group and $R^2$ represents an aryl group that may have a substituent group).

In the formula (1) given above, the alkyl groups represented by $R^1$ include, for example, normal or branched saturated hydrocarbon groups of carbon number in the range of 1–8, such as methyl, ethyl, n-propyl, iso-propyl, n-butyl, iso-butyl, sec-butyl, tert-butyl, pentyl, hexyl, heptyl, octyl, iso-octyl, and 2-ethylhexyl, and alicyclic saturated hydrocarbon groups of carbon number in the range of 5–10, such as cyclohexyl and cyclododecyl.

In the formula (1) given above, aryl groups that may have a substituent group represented by $R^2$ include, for example, aryl groups of carbon number in the range of 6–18, such as phenyl, tolyl, xylyl, biphenyl, naphthyl, anthryl, and phenanthryl. The substituent groups include, for example, a hydroxyl group, a halogen atom (e.g. chlorine, fluorine, bromine, and iodine), a cyano group, an amino group, a carboxyl group, an alkoxyl group (e.g. alkoxyl group of the carbon number in the range of 1–4, such as methoxy, ethoxy, propoxy, and butoxy), an aryloxy group (e.g. a phenoxy group), an alkylthio group (e.g. alkylthio group of the carbon number in the range of 1–4, such as methylthio, ethylthio, propylthio, and butylthio), and an arylthio group (e.g. a phenylthio group). The number of substituent groups per identical groups or different groups may be from one to five, or preferably from one to three.

To be more specific, methylphenyl carbonate is preferably used as the alkylaryl carbonate.

The alkylaryl carbonates cited above can be produced easily by using any known methods, including, for example, a method for producing alkylaryl carbonate by the ester exchange reaction of dialkyl carbonate and phenol or derivatives thereof as described by Japanese Patent No. 1519075, and a method for producing alkylaryl carbonate from aryl chloroformate and alkyl alcohol as described by J. Org. Chem. 57,3237 (1992).

In the present invention, the reaction solution produced by the producing method mentioned above may be used, or the crude material containing alkylaryl carbonate may be used, as it is without any need to use alkylaryl carbonate purified by high-level purification such as recrystallization and fraction.

For example, when alkylaryl carbonate is produced from dialkyl carbonate and phenol or derivatives thereof, crude material containing not less than 1 weight %, or preferably 10–100 weight %, of alkylaryl carbonate produced by the ester exchange reaction of dialkyl carbonate and phenol or derivatives thereof may be used as the alkylaryl carbonate of the producing method of the present invention.

When considering that alkylphenyl carbonate is produced by the reaction of dialkyl carbonate and phenol, as mentioned above, it is feasible to produce carbamates in the method mentioned later, for example, by adding amine in the presence of dialkyl carbonate and phenol or by mixing dialkyl carbonate, phenol and amine.

In the method for producing carbamates of the present invention, the nonaromatic amine mentioned above is allowed to react with the alkylaryl carbonate mentioned above. The nonaromatic amine is allowed to react with alkylaryl carbonate, for example, in the manner that nonaromatic amine and alkylaryl carbonate are charged in a reaction vessel in a predetermined proportion given below under mild conditions and, if needed, a reaction solvent is added thereto.

An amount of alkylaryl carbonate charged may be equivalent molar to or more than the number of moles of animo group of the nonaromatic amine. Due to this, alkylaryl carbonate itself may be used as a reaction solvent in this reaction. To be more specific, the amount of alkylaryl carbonate charged is commonly in the order of 1–50 times, or preferably 1.01–30 times, or further preferably 1.02–15 times, as much as the number of moles corresponding to the number of amino group of nonaromatic amine. If the amount of alkylaryl carbonate charged is more than that, then a considerable amount of energy will be consumed in the subsequent separation process or purification process, then providing inadequateness for industrial production. On the other hand, if the amount of alkylaryl carbonate charged is less than that, then there will be provided the result that the rate of reaction decreases as the reaction proceeds.

The reaction solvent is not necessarily needed for this reaction, but the blending of the reaction solvent can provide improved operability. No particular limitation is imposed on the reaction solvent, as long as it is inactive to or is less-reactive to nonaromatic amine and alkylaryl carbonate. The reaction solvents that may be used include, for example, aliphatic alcohols (e.g. methanol, ethanol, n-propanol, iso-propanol, n-butanol, and iso-butanol), aliphatic hydrocarbons (e.g. hexane, pentane, petroleum ether, ligroin, cyclododecane, and decalins), aromatic hydrocarbons (e.g. benzene, toluene, xylene, ethylbenzene, isopropylbenzene, butylbenzene, cyclohexylbenzene, tetralin, chlorobenzene, o-dichlorobenzene, methylnaphthalene, chloronaphthalene, dibenzyltoluene, triphenylmethane, phenylnaphthalene, biphenyl, diethyl biphenyl, and triethyl biphenyl), ethers (e.g. diethyl ether, diisopropyl ether, dibutyl ether, anisole, diphenyl ether, tetrahydrofuran, ethylene glycol dimethyl ether, ethylene glycol diethyl ether, ethylene glycol dibutyl ether, diethylene glycol dimethyl ether, and diethylene glycol diethyl ether), esters (e.g. ethyl acetate, butyl acetate, amyl acetate, dioctyl phthalate, didesyl phthalate, and didodecyl phthalate), nitriles (e.g. acetonitrile, propionitrile, adiponitrile, and benzonitrile), aliphatic halogenated hydrocarbons (e.g. methylene chloride, chloroform, 1,2-dichloroethane, 1,2-dichloropropane, and 1,4-dichlorobutane), amides (e.g. dimethylformamide, and dimethylacetamide), nitro compounds (e.g. nitromethane, and nitrobenzene), phenol or derivatives thereof (e.g. phenol and cresol), carboic acid esters (e.g. dimethyl carbonate, diethyl carbonate, dipropyl carbonate, and dibutyl carbonate), heat medium oils for general use (e.g. Therm-S series, 200S, 300, 600, 700, 800, 900, 1000S (Name of articles) available from Nippon Steel Chemical Co., Ltd., and Neo SK-OIL 1300, 1400, 170, 240, 330, KSK-OIL 260, 280 (Name of articles) available from Soken Chemical & Engineering Co., Ltd.), N-methyl pyrrolizinone, N,N-dimethyl imidazolidinone, dimethyl sulfoxide, and water.

Among these reaction solvents, aliphatic alcohols, aliphatic hydrocarbons, aromatic hydrocarbons, phenols, and carboic acid esters are preferably used in terms of economical efficiency and operability. These reaction solvents may be used singly or in combination of two or more.

There is no particular limitation to an amount of reaction solvent used, as long as it is sufficient for the carbamates as a reaction product to be dissolved. Industrially, the amount of reaction solvent used should preferably be minimized as much as possible in view that it is necessary to recover the reaction solvent from the reaction solution and the energy consumed for the recovery can be reduced as much as possible, as well as in view that when a large amount of reaction solvent is used, substrate concentration on the reaction decreases and the rate of reaction decreases. To be more specific, the amount of the reaction solvent used is usually in the range of 0.01 to 50 parts by weight, or preferably in the range of 0.1 to 10 parts by weight per part by weight of nonaromatic amine.

In this reaction, reaction temperature varies, depending on kinds of raw material, that is, nonaromatic amine and alkylaryl carbonate, and of reaction solvent, though a reaction temperature is, for example, in the range of 0–200° C., or preferably 20–150° C., or further preferably 30–100° C.

The reaction may be carried out in any adequate atmospheric pressure, under an increased pressure or a reduced pressure, without any particular limitation.

This reaction proceeds without catalyst, but a catalyst may be added, if desired. The catalysts that may be used, include, for example, known carbamate preparation catalysts and ester exchange catalysts, such as Lewis acid, alkali metal salt, alkali earth metal salt, salts of the group III and IV metals, a nitrogen-containing compound, transition metal salt, or a complex thereof.

This reaction can be carried out by agitating or mixing nonaromatic amine and alkylaryl carbonate in the reaction vessel under the conditions mentioned above. To be more specific, for example, nonaromatic amine may be dropped in alkylaryl carbonate and mixed by stirring. This permits alkyl carbamate to be produced with high selectivity and at high yield under temperate conditions. As a result of this, for example, when nonaromatic amine and alkylaryl carbonate are allowed to react with each other without catalyst, this reaction provides the result that the reaction solution after the end of the reaction contains excess (unreacted) alkylaryl carbonate, reaction solvent, reaction product of carbamate expressed by the general formula (2) given below:

$$(R^1OCONH)nR^3 \quad (2)$$

(where $R^1$ represents $R^1$ of the formula (1) given above; $R^3$ represents residue of nonaromatic amine; and n represents the number of amino group of the nonaromatic amine), and the by-product of aryl alcohol expressed by the general formula (3) given below:

$$R^2\text{—OH} \quad (3)$$

(where $R^2$ represents $R^2$ of the formula (1) given above).

These excess (unreacted) alkylaryl carbonate, reaction solvent and aryl alcohol are recovered by distillation and separation and thereby the carbamates produced are separated easily. This reaction usually requires no after-treatment processes, such as separation of catalyst. The carbamates obtained may be further purified by washing, neutralization, recrystallization, distillation, sublimation, column chromatography or the like, if needed.

Thus, this producing method enables alkyl carbamates to be produced with high selectivity and at high yield simply by substantially blending nonaromatic amine and alkylaryl carbonate. Besides, it requires simple equipment and facility and requires no complicated after-treatment process. Hence, the method of the present invention can produce the carbamates at low costs and with efficiency.

The present invention includes a method for producing isocyanates by thermally decomposing the carbamates obtained by the method for producing carbamates described above.

According to the method for producing isocyanates of the present invention, the carbamates obtained by the method for producing carbamates described above is thermally decomposed to thereby produce isocyanate expressed by the following general formula (4) corresponding to the nonaromatic amine described above:

$$R^3\text{—(NCO)n} \quad (4)$$

(where $R^3$ represents $R^3$ of the formula (2) given above, and n represents n of the formula (2) given above), and the by-product of alkyl alcohol expressed by the following formula (5):

$$R^1\text{—OH} \quad (5)$$

(where $R^1$ represents $R^1$ of the formula (1) given above).

No particular limitation is imposed on the thermal decomposition. Known decomposition methods, such as a liquid phase method and a vapor phase method, can be used. Preferably, the thermal decomposition is carried out in the liquid phase method, or rather, in the reaction distillation in which the alkyl alcohol produced as a by-product in the thermal decomposition is separated from the system.

The thermal decomposition temperature is usually 350° C. at highest, or preferably in the range of 80–350° C., or further preferably in the range of 100–300° C. At the thermal decomposition temperature lower than 80° C., there is the possibility that the rate of reaction suitable for practical use may not be obtained. At the thermal decomposition temperature higher than 350° C. on the other hand, there is the possibility that undesired side reaction, such as polymerization of isocyanates, may occur. Also, it is preferable that the pressure at the thermal decomposition reaction is a pressure for allowing the alkyl alcohol produced to be vaporized in the thermal decomposition temperature specified above. The pressure is preferably in the range of 0.133–90 kPa in terms of equipment and use and profits suitable for practical use.

Though purified carbamates is good enough for the carbamates used in the thermal decomposition, the crude material of carbamates obtained by the recovery and separation of the aryl alcohol after the end of the reaction may continue to be thermally decomposed.

Further, catalyst and inactive solvent may be added, if needed. The catalyst and inactive solvent may be added at the time when the reaction for preparation of carbamates is carried out, around the time when the distillation and separation is carried out after the end of the reaction, or around the time when the carbamates is separated, though it depends on the kinds of the catalyst and inactive solvent.

At least one compound of a metal, oxide, halogenide, carboxylate, phosphate, and organic metallic compound, selected from the group consisting of Sn, Sb, Fe, Co, Ni, Cu, Cr, Ti, Pb, Mo and Mn, used for the reaction of isocyanate and hydroxyl group for preparation of urethane, is used as the decomposition catalyst used for the thermal decomposition. Of these materials, Fe, Sn, Co, Sb and Mn are preferably used in this thermal decomposition, because they develop the effect of suppressing the production of the by-product.

Metallic catalysts of Sn that may be used include, for example, tin oxide, tin chloride, tin bromide, tin iodide, tin formate, tin acetate, tin oxalate, tin octylate, tin stearate, tin oleate, tin phosphate, dibutyltin dichloride, dibutyltin dilaurate, and 1,1,3,3-Tetrabutyl-1,3-dilauryloxydistannoxane.

Metallic catalysts of Fe, Co, Sb and Mn include, for example, acetate, benzoate, naphthenate, and acetylacetonate thereof.

It is to be noted that an amount of catalyst used to reaction is preferably in the range of 0.0001–5 weight %, or preferably in the range of 0.001–1 weight % per reaction solvent, as a metal or compound thereof.

Also, the inactive solvent is inactive at least to carbamates and isocyanates and it is preferable that the inactive solvent is also higher in boiling point than isocyanates produced, for producing the thermal decomposition reaction with efficiency. The inactive solvents that may be used include, for example, esters, such as dioctyl phthalate, didecyl phthalate, and didodecyl phthalate, and aromatic hydrocarbons or aliphatic hydrocarbons used regularly as heating medium, such as dibenzyltoluene, triphenylmethane, phenylnaphthalene, biphenyl, diethylbiphenyl, and triethylbiphenyl. An amount of inactive solvent used is in the range of 0.001–100 parts by weight, or preferably 0.01–80 parts by weight, or further preferably 0.1–50 parts by weight, per part by weight of carbamates. The thermal decomposition reaction may be carried out by a batch reaction process wherein carbamates, the catalyst and the inactive solvent are charged as a batch, or by a continuous reaction process wherein carbamates are charged in the inactive solvent containing the catalyst under reduced pressure.

Thus, in this thermal decomposition reaction, the carbamates obtained in the manner mentioned above is thermally decomposed and thereby the isocyanates corresponding to the nonaromatic amines is produced, as mentioned above. Consequently, for example, polyisocyanates industrially used as raw material of polyurethane can be produced in a simple manner and with efficiency.

While there has been described the method for producing carbamates and the method for producing isocyanates so far, the production method of the present invention may include some additional known processes, such as a head end process, such as a dehydration process, an intermediate process, or an after-treatment process, such as a purification process and a recovery process.

EXAMPLES

While in the following, the present invention will be described in further detail with reference to Examples, the present invention is not limited to any Examples.

Example 1

After air was substituted with nitrogen in a 200 mL four-necked glass flask having a reflux condenser, a thermometer, a nitrogen inlet adapter, a dropping funnel, and an agitator, 45.6 g (0.30 mol) of methylphenyl carbonate and 58.8 g of methanol were charged in the flask and then 11.6 g (0.10 mol) of 1,6-hexamethylenediamine was dropped therein under stirring at room temperature. Thereafter, those was allowed to react with each other at 50° C. for three hours and, thereafter, a part of the reaction mixture was taken for sampling and the sample was titrated potentiometrically with 1N hydrochloric acid. The result was that the 1,6-hexamethylenediamine conversion rate was 99.5% or more. Also, from the quantitative analysis of the reaction mixture using a gas chromatography it was found that 1,6-bis (methoxycarbonylamino)hexane was produced at the yield of 99.9%.

Sequentially, after the reaction mixture was transferred into a 200 mL flask having a capillary, a thermometer, and a distilling head, the flask was heated under reduced pressure (0.67 kPa) to distill away a volatile portion of the reaction mixture. As a result of this, 23.2 g of crude crystal of 1,6-bis(methoxycarbonylamino)hexane was left in the flask. After the crude crystal was dissolved in a small amount of methanol, 90 g of diethyl ether was added in the mixture and fully mixed. Then, the precipitated crystal was filtered. The weight of the crystal after dried was 22.6 g (97.7% of isolation yield).

The isolated crystal was identified by using a FT-IR, a MS spectrum, and a $^1$H-NMR. It was observed from the IR spectrum that a N—H stretching 3335 cm$^{-1}$, a C=O stretching 1686 cm$^{-1}$, and a N—H deformation vibration 1530 cm$^{-1}$. From the MS spectrum (M+)=232 was observed. The spectrum of $^1$H-NMR are shown below.

$^1$H-NMR spectrum (CDCl$_3$, TMS; ppm)

1.35 (t, 4H)

1.50 (m, 4H)

3.15 (m, 4H)

3.70 (s, 6H)

4.65–4.85 (b, 2H)

Example 2

After air was substituted with nitrogen in a 200 mL four-necked glass flask having a reflux condenser, a thermometer, a nitrogen inlet adapter, a dropping funnel, and an agitator, 76.1 g (0.30 mol) of crude methylphenyl carbonate (a reaction solution synthesized by the ester exchange reaction of dimethyl carbonate with phenol and simple-distilled and having a mixture of 60 parts by weight of methylphenyl carbonate, 26 parts by weight of phenol, and 9 parts by weight of dimethyl carbonate of a composition ratio measured by the gas chromatograph) and 28.5 g of methanol were charged in the flask and then 11.6 g (0.10 mol) of 1,6-hexamethylenediamine was dropped therein under stirring at room temperature. Thereafter, those were allowed to react with each other at 50° C. for four hours and, thereafter, a part of the reaction mixture was taken for sampling and the sample was titrated potentiometrically with 1N hydrochloric acid. The result was that the 1,6-hexamethylenediamine conversion rate was 99.5% or more. Also, from the quantitative analysis of the reaction mixture using the gas chromatography, it was found that 1,6-bis (methoxycarbonylamino)hexane was produced at the yield of 99.9%.

Example 3

After air was substituted with nitrogen in a 200 mL four-necked glass flask having a reflux condenser, a thermometer, a nitrogen inlet adapter, a dropping funnel, and an agitator, 45.6 g (0.30 mol) of methylphenyl carbonate and 63.3 g of methanol were charged in the flask and then 13.6 g (0.10 mol) of 1,3-bis(aminomethyl)benzene was dropped therein under stirring at room temperature. Thereafter, those were allowed to react with each other at 60° C. for ten hours and, thereafter, a part of the reaction mixture was taken for sampling and the sample was titrated potentiometrically with 1N hydrochloric acid. The result was that the 1,3-bis (aminomethyl)benzene conversion rate was 99.0% or more. Also, from the quantitative analysis of the reaction mixture using the gas chromatography, it was found that 1,3-bis (methoxycarbonyl aminomethyl)benzene was produced at the yield of 99.7%.

Example 4

After air was substituted with nitrogen in a 200 mL four-necked glass flask having a reflux condenser, a thermometer, a nitrogen inlet adapter, a dropping funnel, and an agitator, 45.6 g (0.30 mol) of methylphenyl carbonate and 68.1 g of methanol were charged in the flask and then 14.2 g (0.10 mol) of 1,3-bis(aminomethyl)cyclohexane was dropped therein under stirring at room temperature. Thereafter, those were allowed to react with each other at 60° C. for eight hours and, thereafter, a part of the reaction mixture was taken for sampling and the sample was titrated potentiometrically with 1N hydrochloric acid. The result was that the 1,3-bis(aminomethyl) cyclohexane conversion rate was 99.0% or more. Also, from the quantitative analysis of the reaction mixture using the gas chromatography, it was found that 1,3-bis(methoxycarbonyl aminomethyl) cyclohexane was produced at the yield of 99.9%.

Example 5

After air was substituted with nitrogen in a 200 mL four-necked glass flask having a reflux condenser, a thermometer, a nitrogen inlet adapter, a dropping funnel, and an agitator, 82.2 g (0.54 mol) of methylphenyl carbonate was charged in the flask and then 17.0 g (0.10 mol) of isophorone diamine was dropped therein under stirring at room temperature. Thereafter, those were allowed to react with each other at 60° C. for six hours and, thereafter, a part of the reaction mixture was taken for sampling and the sample was titrated potentiometrically with 1N hydrochloric acid. The result was that the isophorone diamine conversion rate was 99.0% or more. Also, from the quantitative analysis of the reaction mixture using the gas chromatography, it was found that isophorone dimethyl carbamate was produced at the yield of 99.8%.

Example 6

After air was substituted with nitrogen in a 200 mL four-necked glass flask having a reflux condenser, a thermometer, a nitrogen inlet adapter, a dropping funnel, and an agitator, 45.6 g (0.30 mol) of methylphenyl carbonate and 30 g of toluene were charged in the flask and then 40.7 g (0.15 mol) of octadecylamine was dropped therein under stirring at room temperature. Thereafter, those were allowed to react with each other at 60° C. for two hours and, thereafter, a part of the reaction mixture was taken for sampling and the sample was titrated potentiometrically with 1N hydrochloric acid. The result was that the octadecylamine conversion rate was 99.0% or more. Also, from the quantitative analysis of the reaction mixture using the gas chromatography, it was found that methyl N-octadecylcarbamate was produced at the yield of 99.5%.

Example 7

After air was substituted with nitrogen in a 200 mL four-necked glass flask having a reflux condenser, a thermometer, a nitrogen inlet adapter, a dropping funnel, and an agitator, 45.6 g (0.30 mol) of methylphenyl carbonate and 30 g of toluene were charged in the flask and then 19.4 g (0.15 mol) of octylamine was dropped therein under stirring at room temperature. Thereafter, those were allowed to react with each other at 60° C. for two hours and, thereafter, a part of the reaction mixture was taken for sampling and the sample was titrated potentiometrically with 1N hydrochloric acid. The result was that the octylamine conversion rate was 99.0% or more. Also, from the quantitative analysis of the reaction mixture using the gas chromatography, it was found that methyl N-octylcarbamate was produced at the yield of 99.5%.

Example 8

After air was substituted with nitrogen in a 200 mL four-necked glass flask having a reflux condenser, a thermometer, a nitrogen inlet adapter, a dropping funnel, and an agitator, 80.2 g (0.53 mol) of methylphenyl carbonate was charged in the flask and then 18.0 g (0.10 mol) of 1,2-bis (2-aminoethylthio)ethane was dropped therein under stirring at room temperature. Thereafter, those were allowed to react with each other at 60° C. for five hours and, thereafter, a part of the reaction mixture was taken for sampling and the sample was titrated potentiometrically with 1N hydrochloric acid. The result was that the 1,2-bis(2-aminoethylthio) ethane conversion rate was 99.0% or more. Also, from the quantitative analysis of the reaction mixture using the gas chromatography, it was found that 1,2-bis(2-methoxycarbonyl aminoethylthio)ethane was produced at the yield of 99.0%.

Example 9

After 50 ml of 2M-NaOH aqueous solution and 8.9 g (0.10 mol) of sarcosine were charged in a 200 mL four-necked glass flask having a reflux condenser, a thermometer, a nitrogen inlet adapter, and an agitator and were stirred at room temperature so that the sarcosine can be completely dissolved in the solution to prepare a solution of sarcosine sodium salt. Sequentially, 45.6 g (0.30 mol) of methylphenyl carbonate was added to the solution and was allowed to react with it at 50° C. for eight hours under stirring vigorously. Thereafter, the reaction mixture was poured into a separating funnel to separate an organic layer and hydrochloric acid was added to the aqueous layer to adjust the pH of the aqueous layer to pH3. The aqueous layer was extracted with ethyl acetate and ethyl acetate was washed with water. From the quantitative analysis of the ethyl acetate solution using the gas chromatography, it was found that N-methoxycarbonyl sarcosine was produced at the yield of 90.5%.

Example 10

After 50 ml of 2M-NaOH aqueous solution and 7.1 g (0.10 mol) of glycin were charged in a 200 mL four-necked glass flask having a reflux condenser, a thermometer, a nitrogen inlet adapter, and an agitator and were stirred at room temperature so that the glycin can be completely dissolved in the solution to prepare a solution of glycin sodium salt. Sequentially, 45.6 g (0.30 mol) of methylphenyl carbonate was added to the solution and was allowed to react with it at 50° C. for eight hours under stirring vigorously. Thereafter, the reaction mixture was poured into a separating funnel to separate an organic layer and hydrochloric acid was added to the aqueous layer to adjust the pH of the aqueous layer to pH3. The aqueous layer was extracted with ethyl acetate and ethyl acetate was washed with water. From the quantitative analysis of the ethyl acetate solution using the gas chromatography, it was found that N-methoxycarbonyl glycin was produced at the yield of 91.4%.

Example 11

After 50 ml of 2M-NaOH aqueous solution and 8.9 g (0.10 mol) of L-alanine were charged in a 200 mL four-necked glass flask having a reflux condenser, a thermometer, a nitrogen inlet adapter, and an agitator and were stirred at room temperature so that the L-alanine can be completely dissolved in the solution to prepare a solution of L-alanine sodium salt. Sequentially, 45.6 g (0.30 mol) of methylphenyl carbonate was added to the solution and was allowed to react with it at 50° C. for eight hours under stirring vigorously. Thereafter, the reaction mixture was poured into a separating funnel to separate an organic layer and hydrochloric acid was added to the aqueous layer to adjust the pH of the aqueous layer to pH3. The aqueous layer was extracted with ethyl acetate and ethyl acetate was washed with water. From the quantitative analysis of the ethyl acetate solution using the gas chromatography, it was found that N-methoxycarbonyl L-alanine was produced at the yield of 91.5%.

Comparative Example 1

After air was substituted with nitrogen in a 200 mL four-necked glass flask having a reflux condenser, a thermometer, a nitrogen inlet adapter, a dropping funnel, and an agitator, 54.0 g (0.60 mol) of dimethyl carbonate and 58.8 g of methanol were charged in the flask and then 11.6 g (0.10 mol) of 1,6-hexamethylenediamine was dropped therein under stirring at room temperature. Thereafter, those was allowed to react with each other at 70° C. for sixteen hours and, thereafter, a part of the reaction mixture was taken for sampling and the sample was titrated potentiometrically with 1N hydrochloric acid. The result was that the 1,6-hexamethylenediamine conversion rate was 71.9%. Also, from the quantitative analysis of the reaction mixture using the gas chromatography, it was found that 1,6-bis(methoxycarbonylamino)hexane was produced at the yield of 41.6%. It was also found that 5.6% of N-methyl compound was produced.

Example 12

A 500 mL flask having a capillary, a thermometer and a fractioning column with a condenser was used as the reactor vessel. With hot water of 60° C. flown through the condenser, a receiver is connected with a vacuum line through a cold trap cooled with cold ethanol. After the reaction mixture of 1,6-bis(methoxycarbonylamino)hexane obtained in Example 1 was poured into the flask, the flask was set in an oil bath. Then, the flask was reduced in pressure to 0.67 kPa and the oil bath was increased in temperature to 90° C., to distill away a volatile portion of the reaction mixture, such as unreacted methylphenyl carbonate and the by-product of phenol.

Then, after the pressure in the reaction system was returned to the normal pressure, 100 g of Therm S 1000S (available from Nippon Steel Chemical Co., Ltd.) and 0.15 g of dibutyltin dilaurate were charged in the flask. Then, the reaction system was substituted with nitrogen and then was reduced in pressure to 3.3 kPa and the oil bath was increased in temperature to 250° C., so that the contents are allowed to be decomposed for an hour. From the quantitative analysis of the distillate collected in the receiver using a gas chromatography after the end of the reaction, it was found that 12.5 g (74.1%) of 1,6-hexamethylenediisocyanate and 4.6 g (23.0%) of monoisocyanate were produced.

Example 13

The 1,6-bis(methoxycarbonylamino)hexane obtained in Example 2 was subjected to the thermal decomposition reaction in the same manner as in Example 12 to obtain 12.6 g (74.9%) of 1,6-hexamethylenediisocyanate and 4.4 g (22.0%) of monoisocyanate.

Example 14

The 1,3-bis(methoxycarbonylaminomethyl)cyclohexane obtained in Example 4 was subjected to the thermal decomposition reaction in the same manner as in Example 12 to obtain 14.2 g (73.1%) of 1,3-bis(isocyanatomethyl)cyclohexane and 4.7 g (20.9%) of monoisocyanate.

Comparative Example 2

After air was substituted with nitrogen in a 300 mL four-necked glass flask having a reflux condenser, a thermometer, a nitrogen inlet adapter, a dropping funnel, and an agitator, 11.6 g (0.10 mol) of 1,6-hexamethylenediamine and 72.0 g (0.80 mol) of dimethyl carbonate were charged in the flask. The flask was increased in temperature to 70° C., while the contents are stirred. Sequentially, 1.5 g of 28% methanol solution of sodium methylate was added for 30 minutes. Further, those were allowed to react with each other at 70° C. for an hour and, thereafter, a part of the reaction mixture was taken for sampling and the sample was titrated potentiometrically with 1N hydrochloric acid. The result was that the 1,6-hexamethylenediamine conversion rate was 99.5%. Also, from the quantitative analysis of the reaction mixture using the gas chromatography, it was found that 1,6-bis(methoxycarbonylamino)hexane was produced at the yield of 99.5%.

Then, the 1,6-bis(methoxycarbonylamino)hexane thus obtained was thermally decomposed in the following manner. A 500 mL flask having a capillary, a thermometer, a fractioning column with a condenser was used as the reactor vessel. With hot water of 60° C. flown through the condenser, a receiver is connected with a vacuum line through a cold trap cooled with cold ethanol. After the reaction mixture of 1,6-bis(methoxycarbonylamino)hexane obtained was poured into the flask, the flask was set in an oil bath. Then, the flask was reduced in pressure to 0.67 kPa and the oil bath was increased in temperature to 90° C., to distill away a volatile portion of the reaction mixture, such as unreacted methyl carbonate and the by-product of methanol.

Then, after the pressure in the reaction system was returned to the normal pressure, 100 g of Therm S 1000S (available from Nippon Steel Chemical Co., Ltd.) and 0.15 g of dibutyltin dilaurate were charged in the flask. Then, the reaction system was substituted with nitrogen and then was reduced in pressure to 3.3 kPa and the oil bath was increased in temperature to 250° C. This condition was kept for an hour. During the time, it was found that the 1,6-hexamethylenediisocyanate was not distilled and some solid compound was produced in the flask.

While the illustrative embodiments of the present invention are provided in the above description, such is for illustrative purpose only and it is not to be construed restrictively. Modification and variation of the present invention that will be obvious to those skilled in the art is to be covered by the following claims.

What is claimed is:

1. A method for producing carbamates, wherein a nonaromatic amine selected from the group consisting of aliphatic amine, alicyclic amine, and aralkyl amine is allowed to react with methylphenyl carbonate in the absence of a catalyst.

2. The method for producing carbamates according to claim 1, wherein the methylphenyl carbonate is a crude material containing at least 1 weight % of methylphenyl carbonate, which is obtained by an ester exchange reaction of dimethyl carbonate with phenol or a derivative thereof.

3. The method for producing carbamates according to claim 1, wherein the nonaromatic amine is at least one compound selected from the group consisting of 1,6-hexamethylenediamine, isophorone diamine, 1,3-bis(aminomethyl)cyclohexane, 1,4-bis(aminomethyl)cyclohexane, 4,4'-methylenebis(cyclohexaneamine), 2,5-bis(aminomethyl)bicyclo[2,2,1]heptane, 2,6-bis(aminomethyl)bicyclo[2,2,1]heptane, 1,3-bis(aminomethyl)benzene and 1,4-bis(aminomethyl)benzene.

4. The method for producing carbamates according to claim 1, wherein the nonaromatic amine is an amino acid or derivative thereof.

5. A method for producing isocyanates, which comprises a step of producing carbamates by reacting a nonaromatic amine selected from the group consisting of aliphatic amine, alicyclic amine, and aralkyl amine with methylphenyl carbonate in the absence of a catalyst and a step of producing isocyanates by thermally decomposing the carbamates.

* * * * *